(12) United States Patent
Wiehn et al.

(10) Patent No.: US 12,409,054 B2
(45) Date of Patent: Sep. 9, 2025

(54) PIVOT DELIVERY SYSTEM FOR IMPLANTABLE MEDICAL DEVICE

(71) Applicant: W. L. Gore & Associates, Inc., Newark, DE (US)

(72) Inventors: Michael T. Wiehn, Flagstaff, AZ (US); Taylor B. Wiehn, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1097 days.

(21) Appl. No.: 17/268,040

(22) PCT Filed: Aug. 31, 2018

(86) PCT No.: PCT/US2018/049057
§ 371 (c)(1),
(2) Date: Feb. 11, 2021

(87) PCT Pub. No.: WO2020/046365
PCT Pub. Date: Mar. 5, 2020

(65) Prior Publication Data
US 2021/0244553 A1 Aug. 12, 2021

(51) Int. Cl.
*A61F 2/95* (2013.01)
*A61F 2/07* (2013.01)
*A61M 25/01* (2006.01)

(52) U.S. Cl.
CPC .............. *A61F 2/95* (2013.01); *A61F 2/07* (2013.01); *A61F 2002/9511* (2013.01); *A61M 25/0147* (2013.01); *A61M 2025/015* (2013.01)

(58) Field of Classification Search
CPC .. A61F 2/9522; A61F 2/95; A61F 2/07; A61F 2/011; A61B 17/00; A61B 17/12118; A61M 25/0133
See application file for complete search history.

(56) References Cited

U.S. PATENT DOCUMENTS

| 1,355,373 | A | 10/1920 | Dell |
| 1,506,432 | A | 8/1924 | Kimmel |
| 1,851,314 | A | 3/1932 | Knoche |
| 3,625,451 | A | 12/1971 | Anderson |
| 3,915,167 | A | 10/1975 | Waterman |
| 3,953,566 | A | 4/1976 | Gore |
| 4,187,390 | A | 2/1980 | Gore |

(Continued)

FOREIGN PATENT DOCUMENTS

| CN | 101554343 A | 10/2009 |
| CN | 101780306 A | 7/2010 |

(Continued)

OTHER PUBLICATIONS

International Search Report and Written Opinion received for PCT Patent Application No. PCT/US2018/049057, mailed on Apr. 23, 2019, 14 pages.

(Continued)

*Primary Examiner* — Rebecca S Preston

(57) ABSTRACT

Various aspects of the present disclosure are directed toward apparatuses, systems, and methods that include steering an implantable medical device. The apparatuses, systems, and methods may include an actuation line; a pivot coupled to the implantable medical device; and a tether attached at one end to the actuation line and arranged through the pivot.

19 Claims, 7 Drawing Sheets

(56) References Cited

U.S. PATENT DOCUMENTS

| | | |
|---|---|---|
| 4,503,569 A | 3/1985 | Dotter |
| 4,512,338 A | 4/1985 | Balko et al. |
| 4,655,246 A | 4/1987 | Phlipot et al. |
| 4,858,810 A | 8/1989 | Intlekofer et al. |
| 4,990,155 A | 2/1991 | Wilkoff |
| 5,035,706 A | 7/1991 | Giantureo et al. |
| 5,037,427 A | 8/1991 | Harada et al. |
| 5,147,370 A | 9/1992 | Mcnamara et al. |
| 5,211,658 A | 5/1993 | Clouse |
| 5,217,486 A | 6/1993 | Rice et al. |
| 5,221,261 A | 6/1993 | Termin et al. |
| 5,276,276 A | 1/1994 | Gunn |
| 5,325,746 A | 7/1994 | Anderson |
| 5,344,427 A | 9/1994 | Cottenceau et al. |
| 5,491,704 A | 2/1996 | Duron |
| 5,527,338 A | 6/1996 | Purdy |
| 5,554,183 A | 9/1996 | Nazari |
| 5,562,726 A | 10/1996 | Chuter |
| 5,577,299 A | 11/1996 | Thompson et al. |
| 5,693,083 A | 12/1997 | Baker et al. |
| 5,707,376 A | 1/1998 | Kavteladze et al. |
| 5,709,704 A | 1/1998 | Nott et al. |
| 5,713,917 A | 2/1998 | Leonhardt et al. |
| 5,713,948 A | 2/1998 | Uflacker |
| 5,720,776 A | 2/1998 | Chuter et al. |
| 5,725,552 A | 3/1998 | Kotula et al. |
| 5,776,141 A | 7/1998 | Klein et al. |
| 5,776,186 A | 7/1998 | Uflacker |
| 5,782,909 A | 7/1998 | Quiachon et al. |
| 5,843,162 A | 12/1998 | Inoue |
| 5,873,906 A | 2/1999 | Lau et al. |
| 5,904,703 A | 5/1999 | Gilson |
| 5,961,546 A | 10/1999 | Robinson et al. |
| 6,013,093 A | 1/2000 | Nott et al. |
| 6,015,431 A | 1/2000 | Thornton et al. |
| 6,019,785 A | 2/2000 | Strecker |
| 6,042,588 A | 3/2000 | Munsinger et al. |
| 6,042,602 A | 3/2000 | Wells |
| 6,143,021 A | 11/2000 | Staehle |
| 6,152,144 A | 11/2000 | Lesh et al. |
| 6,165,195 A | 12/2000 | Wilson |
| 6,203,550 B1 | 3/2001 | Olson |
| 6,214,025 B1 | 4/2001 | Thistle et al. |
| 6,224,627 B1 | 5/2001 | Armstrong et al. |
| 6,231,561 B1 | 5/2001 | Frazier et al. |
| 6,231,581 B1 | 5/2001 | Shank et al. |
| 6,231,589 B1 | 5/2001 | Wessman et al. |
| 6,264,671 B1 | 7/2001 | Stack et al. |
| 6,273,900 B1 | 8/2001 | Nott et al. |
| 6,302,891 B1 | 10/2001 | Nadal |
| 6,312,454 B1 | 11/2001 | Stoeckel et al. |
| 6,322,585 B1 | 11/2001 | Khosravi et al. |
| 6,328,727 B1 | 12/2001 | Frazier et al. |
| 6,346,117 B1 | 2/2002 | Greenhalgh |
| 6,352,561 B1 | 3/2002 | Leopold et al. |
| 6,451,051 B2 | 9/2002 | Drasler et al. |
| 6,475,234 B1 | 11/2002 | Richter et al. |
| 6,485,513 B1 | 11/2002 | Fan |
| 6,491,704 B2 | 12/2002 | Gifford et al. |
| 6,524,335 B1 | 2/2003 | Hartley et al. |
| 6,527,779 B1 | 3/2003 | Rourke |
| 6,551,303 B1 | 4/2003 | Van et al. |
| 6,551,350 B1 | 4/2003 | Thornton et al. |
| 6,572,643 B1 | 6/2003 | Gharibadeh |
| 6,572,646 B1 | 6/2003 | Boylan et al. |
| 6,689,150 B1 | 2/2004 | Vantassel et al. |
| 6,705,563 B2 | 3/2004 | Luo et al. |
| 6,712,836 B1 | 3/2004 | Berg et al. |
| 6,712,842 B1 | 3/2004 | Gifford et al. |
| 6,730,108 B2 | 5/2004 | Van et al. |
| 6,733,521 B2 | 5/2004 | Chobotov et al. |
| 6,743,210 B2 | 6/2004 | Hart et al. |
| 6,746,472 B2 | 6/2004 | Frazier et al. |
| 6,755,854 B2 | 6/2004 | Gillick et al. |
| 6,827,731 B2 | 12/2004 | Armstrong et al. |
| 6,866,669 B2 | 3/2005 | Buzzard et al. |
| 6,884,259 B2 | 4/2005 | Tran et al. |
| 6,911,039 B2 | 6/2005 | Shiu et al. |
| 6,926,732 B2 | 8/2005 | Derus et al. |
| 6,939,352 B2 | 9/2005 | Buzzard et al. |
| 6,945,990 B2 | 9/2005 | Greenan |
| 6,949,113 B2 | 9/2005 | Van et al. |
| 6,974,471 B2 | 12/2005 | Van et al. |
| 6,994,092 B2 | 2/2006 | Van et al. |
| 7,033,368 B2 | 4/2006 | Rourke |
| 7,044,134 B2 | 5/2006 | Khairkhahan et al. |
| 7,049,380 B1 | 5/2006 | Chang et al. |
| 7,052,511 B2 | 5/2006 | Weldon et al. |
| 7,066,951 B2 | 6/2006 | Chobotov |
| 7,081,132 B2 | 7/2006 | Cook et al. |
| 7,122,050 B2 | 10/2006 | Randall et al. |
| 7,128,073 B1 | 10/2006 | Van et al. |
| 7,147,657 B2 | 12/2006 | Chiang et al. |
| 7,147,661 B2 | 12/2006 | Chobotov et al. |
| 7,169,160 B1 | 1/2007 | Middleman et al. |
| 7,198,636 B2 | 4/2007 | Cully et al. |
| 7,208,003 B2 | 4/2007 | Davis et al. |
| 7,252,680 B2 | 8/2007 | Freitag |
| 7,331,992 B2 | 2/2008 | Randall et al. |
| 7,396,359 B1 | 7/2008 | Derowe et al. |
| 7,419,498 B2 | 9/2008 | Opolski et al. |
| 7,462,675 B2 | 12/2008 | Chang et al. |
| 7,555,034 B2 | 6/2009 | Shin et al. |
| 7,566,336 B2 | 7/2009 | Corcoran et al. |
| 7,572,289 B2 | 8/2009 | Sisken et al. |
| 7,601,159 B2 | 10/2009 | Ewers et al. |
| 7,611,528 B2 | 11/2009 | Goodson et al. |
| 7,655,034 B2 | 2/2010 | Mitchell et al. |
| 7,771,455 B2 | 8/2010 | Ken |
| 7,815,591 B2 | 10/2010 | Levine et al. |
| 7,837,724 B2 | 11/2010 | Keeble et al. |
| 7,846,179 B2 | 12/2010 | Belef et al. |
| 7,887,580 B2 | 2/2011 | Randall et al. |
| 7,938,851 B2 | 5/2011 | Olson et al. |
| 7,976,575 B2 | 7/2011 | Hartley |
| 7,998,189 B2 | 8/2011 | Koelbel et al. |
| 8,029,559 B2 | 10/2011 | Sisken et al. |
| 8,043,356 B2 | 10/2011 | Koelbel et al. |
| 8,048,440 B2 | 11/2011 | Chang et al. |
| 8,062,349 B2 | 11/2011 | Moore et al. |
| 8,080,032 B2 | 12/2011 | Van et al. |
| 8,167,927 B2 | 5/2012 | Chobotov |
| 8,231,650 B2 | 7/2012 | Cully et al. |
| 8,241,346 B2 | 8/2012 | Chobotov |
| 8,241,350 B2 | 8/2012 | Randall et al. |
| 8,252,037 B2 | 8/2012 | Styrc et al. |
| 8,257,431 B2 | 9/2012 | Henderson et al. |
| 8,262,671 B2 | 9/2012 | Osypka |
| 8,273,105 B2 | 9/2012 | Cohen et al. |
| 8,287,583 B2 | 10/2012 | Laduca et al. |
| 8,328,861 B2 | 12/2012 | Martin et al. |
| 8,361,135 B2 | 1/2013 | Dittman |
| 8,394,139 B2 | 3/2013 | Roeder et al. |
| 8,424,166 B2 | 4/2013 | Dorneman et al. |
| 8,449,595 B2 | 5/2013 | Ouellette et al. |
| 8,469,990 B2 | 6/2013 | Mcguckin et al. |
| 8,480,725 B2 | 7/2013 | Rasmussen et al. |
| 8,523,897 B2 | 9/2013 | Van et al. |
| 8,529,597 B2 | 9/2013 | Linder et al. |
| 8,685,055 B2 | 4/2014 | Vantassel et al. |
| 8,690,911 B2 | 4/2014 | Miles et al. |
| 8,834,519 B2 | 9/2014 | Van et al. |
| 8,870,947 B2 | 10/2014 | Shaw |
| 8,968,384 B2 | 3/2015 | Pearson et al. |
| 8,979,919 B2 | 3/2015 | Goddard et al. |
| 8,986,363 B2 | 3/2015 | Mchugo et al. |
| 9,060,895 B2 | 6/2015 | Hartley et al. |
| 9,095,466 B2 | 8/2015 | Norris et al. |
| 9,132,025 B2 | 9/2015 | Aristizabal et al. |
| 9,254,204 B2 | 2/2016 | Roeder et al. |
| 9,265,596 B2 | 2/2016 | Shank et al. |
| 9,308,349 B2 | 4/2016 | Rezac et al. |
| 9,351,858 B2 | 5/2016 | Chobotov et al. |
| 9,364,359 B2 | 6/2016 | Crawford et al. |

(56) References Cited

U.S. PATENT DOCUMENTS

| | | | |
|---|---|---|---|
| 9,375,308 B2 | 6/2016 | Norris | |
| 9,387,097 B2 | 7/2016 | Eblacas et al. | |
| 9,498,361 B2 | 11/2016 | Roeder et al. | |
| 9,585,743 B2 | 3/2017 | Cartledge et al. | |
| 9,585,774 B2 | 3/2017 | Aristizabal et al. | |
| 9,681,968 B2 | 6/2017 | Goetz et al. | |
| 9,700,701 B2 | 7/2017 | Benjamin et al. | |
| 9,730,700 B2 | 8/2017 | Herbowy et al. | |
| 9,770,322 B2 | 9/2017 | Burkart et al. | |
| 9,782,282 B2 | 10/2017 | Bloss et al. | |
| 9,782,284 B2 | 10/2017 | Hartley et al. | |
| 9,877,858 B2 * | 1/2018 | Beard | A61F 2/97 |
| 9,937,070 B2 | 4/2018 | Skelton et al. | |
| 9,987,155 B1 | 6/2018 | Sondreaal | |
| 11,123,174 B2 | 9/2021 | Burkart et al. | |
| 11,324,615 B2 | 5/2022 | Bloss et al. | |
| 2001/0034549 A1 | 10/2001 | Bartholf et al. | |
| 2001/0037142 A1 | 11/2001 | Stelter et al. | |
| 2002/0007208 A1 | 1/2002 | Strecker | |
| 2002/0029076 A1 | 3/2002 | Yee | |
| 2002/0029077 A1 | 3/2002 | Leopold et al. | |
| 2002/0040236 A1 | 4/2002 | Lau et al. | |
| 2002/0091439 A1 | 7/2002 | Baker et al. | |
| 2002/0099431 A1 | 7/2002 | Armstrong et al. | |
| 2002/0151953 A1 | 10/2002 | Chobotov et al. | |
| 2003/0088305 A1 | 5/2003 | Van et al. | |
| 2003/0098383 A1 | 5/2003 | Luo et al. | |
| 2003/0149467 A1 | 8/2003 | Linder et al. | |
| 2003/0181942 A1 | 9/2003 | Sutton et al. | |
| 2004/0034366 A1 | 2/2004 | Van et al. | |
| 2004/0054396 A1 | 3/2004 | Hartley et al. | |
| 2004/0063805 A1 | 4/2004 | Pacetti et al. | |
| 2004/0073289 A1 | 4/2004 | Hartley | |
| 2004/0122503 A1 | 6/2004 | Campbell et al. | |
| 2004/0138734 A1 | 7/2004 | Chobotov et al. | |
| 2004/0143315 A1 | 7/2004 | Bruun et al. | |
| 2005/0038470 A1 | 2/2005 | Van et al. | |
| 2005/0049667 A1 | 3/2005 | Arbefeuille et al. | |
| 2005/0070820 A1 | 3/2005 | Boutillette et al. | |
| 2005/0080476 A1 | 4/2005 | Gunderson et al. | |
| 2005/0085890 A1 | 4/2005 | Rasmussen et al. | |
| 2005/0125031 A1 | 6/2005 | Pipenhagen et al. | |
| 2005/0240257 A1 | 10/2005 | Ishimaru et al. | |
| 2006/0004433 A1 | 1/2006 | Greenberg et al. | |
| 2006/0015171 A1 | 1/2006 | Armstrong | |
| 2006/0058833 A1 | 3/2006 | Vancamp et al. | |
| 2006/0155366 A1 | 7/2006 | Laduca et al. | |
| 2006/0198866 A1 | 9/2006 | Chang et al. | |
| 2006/0254569 A1 | 11/2006 | Chipman | |
| 2006/0264980 A1 | 11/2006 | Khairkhahan et al. | |
| 2007/0016281 A1 | 1/2007 | Melsheimer | |
| 2007/0066993 A1 | 3/2007 | Kreidler | |
| 2007/0088424 A1 | 4/2007 | Greenberg et al. | |
| 2007/0100427 A1 | 5/2007 | Perouse | |
| 2007/0162048 A1 | 7/2007 | Quinn et al. | |
| 2007/0167955 A1 | 7/2007 | Arnault et al. | |
| 2007/0198077 A1 | 8/2007 | Cully et al. | |
| 2007/0198078 A1 | 8/2007 | Berra et al. | |
| 2007/0219467 A1 | 9/2007 | Clark et al. | |
| 2007/0225797 A1 | 9/2007 | Krivoruhko | |
| 2007/0248640 A1 | 10/2007 | Karabey et al. | |
| 2007/0249980 A1 | 10/2007 | Carrez et al. | |
| 2007/0255390 A1 | 11/2007 | Ducke et al. | |
| 2007/0270891 A1 | 11/2007 | McGuckin | |
| 2008/0027529 A1 | 1/2008 | Hartley et al. | |
| 2008/0039925 A1 | 2/2008 | Ishimaru et al. | |
| 2008/0114440 A1 | 5/2008 | Hlavka et al. | |
| 2008/0147111 A1 | 6/2008 | Johnson et al. | |
| 2008/0178434 A1 | 7/2008 | Bulanda | |
| 2008/0208329 A1 | 8/2008 | Bishop et al. | |
| 2008/0269785 A1 | 10/2008 | Lampropoulos et al. | |
| 2008/0294234 A1 | 11/2008 | Hartley et al. | |
| 2009/0048656 A1 | 2/2009 | Wen | |
| 2009/0054723 A1 | 2/2009 | Khairkhahan et al. | |
| 2009/0062838 A1 | 3/2009 | Brumleve et al. | |
| 2009/0082844 A1 | 3/2009 | Zacharias et al. | |
| 2009/0099596 A1 | 4/2009 | Mcguckin et al. | |
| 2009/0099640 A1 * | 4/2009 | Weng | A61F 2/95 623/1.11 |
| 2009/0112249 A1 | 4/2009 | Miles et al. | |
| 2009/0171386 A1 | 7/2009 | Amplatz et al. | |
| 2009/0182405 A1 | 7/2009 | Arnault De La Menardiere et al. | |
| 2009/0182407 A1 | 7/2009 | Leanna et al. | |
| 2009/0182411 A1 | 7/2009 | Irwin et al. | |
| 2009/0204198 A1 | 8/2009 | Jensen et al. | |
| 2009/0216308 A1 | 8/2009 | Hartley | |
| 2009/0259291 A1 | 10/2009 | Kolbel et al. | |
| 2009/0299449 A1 | 12/2009 | Styrc | |
| 2010/0016943 A1 | 1/2010 | Chobotov | |
| 2010/0023048 A1 | 1/2010 | Mach | |
| 2010/0057195 A1 | 3/2010 | Roeder et al. | |
| 2010/0082089 A1 | 4/2010 | Quadri et al. | |
| 2010/0094394 A1 | 4/2010 | Beach et al. | |
| 2010/0094401 A1 * | 4/2010 | Kolbel | A61B 17/12118 623/1.13 |
| 2010/0114290 A1 | 5/2010 | Rasmussen et al. | |
| 2010/0145434 A1 | 6/2010 | Thornton et al. | |
| 2010/0211052 A1 | 8/2010 | Brown et al. | |
| 2010/0280591 A1 | 11/2010 | Shin et al. | |
| 2011/0040366 A1 | 2/2011 | Goetz et al. | |
| 2011/0054515 A1 | 3/2011 | Bridgeman et al. | |
| 2011/0054519 A1 | 3/2011 | Neuss | |
| 2011/0066221 A1 | 3/2011 | White et al. | |
| 2011/0094401 A1 | 4/2011 | Möhringer et al. | |
| 2011/0125252 A1 | 5/2011 | Goddard et al. | |
| 2011/0130821 A1 | 6/2011 | Styrc | |
| 2011/0288624 A1 | 11/2011 | Roeder et al. | |
| 2011/0313503 A1 | 12/2011 | Berra et al. | |
| 2012/0022630 A1 | 1/2012 | Martin | |
| 2012/0022638 A1 | 1/2012 | Leewood et al. | |
| 2012/0046652 A1 | 2/2012 | Sokel | |
| 2012/0130473 A1 | 5/2012 | Norris et al. | |
| 2012/0130474 A1 | 5/2012 | Buckley | |
| 2012/0130475 A1 | 5/2012 | Shaw | |
| 2012/0143305 A1 | 6/2012 | Berra et al. | |
| 2012/0172965 A1 | 7/2012 | Kratzberg et al. | |
| 2012/0172968 A1 | 7/2012 | Chuter et al. | |
| 2012/0239133 A1 | 9/2012 | Cartledge et al. | |
| 2012/0283773 A1 | 11/2012 | Van et al. | |
| 2012/0296360 A1 | 11/2012 | Norris et al. | |
| 2012/0323270 A1 | 12/2012 | Lee | |
| 2013/0023981 A1 | 1/2013 | Dierking et al. | |
| 2013/0046371 A1 | 2/2013 | Greenberg et al. | |
| 2013/0073029 A1 | 3/2013 | Shaw | |
| 2013/0123896 A1 | 5/2013 | Bloss et al. | |
| 2013/0138138 A1 | 5/2013 | Clark et al. | |
| 2013/0158647 A1 | 6/2013 | Norris et al. | |
| 2013/0178889 A1 | 7/2013 | Miles et al. | |
| 2013/0245666 A1 | 9/2013 | Larsen et al. | |
| 2013/0245742 A1 | 9/2013 | Norris | |
| 2013/0296912 A1 | 11/2013 | Ottma | |
| 2014/0012303 A1 | 1/2014 | Heipl | |
| 2014/0046360 A1 | 2/2014 | Van et al. | |
| 2014/0180385 A1 | 6/2014 | Majercak | |
| 2014/0194968 A1 | 7/2014 | Zukowski | |
| 2014/0277412 A1 | 9/2014 | Bortlein et al. | |
| 2014/0296908 A1 | 10/2014 | Ottma et al. | |
| 2014/0296909 A1 | 10/2014 | Heipl et al. | |
| 2014/0379019 A1 | 12/2014 | Larsen et al. | |
| 2015/0005809 A1 | 1/2015 | Ayres et al. | |
| 2015/0005810 A1 | 1/2015 | Center et al. | |
| 2015/0051695 A1 | 2/2015 | Shaw | |
| 2015/0305749 A1 | 10/2015 | Alferness | |
| 2015/0313738 A1 | 11/2015 | Cully et al. | |
| 2016/0256301 A1 | 9/2016 | Roeder et al. | |
| 2016/0278782 A1 | 9/2016 | Anderson et al. | |
| 2016/0296352 A1 | 10/2016 | Ryan et al. | |
| 2016/0331382 A1 | 11/2016 | Center et al. | |
| 2017/0056153 A1 | 3/2017 | Vinluan et al. | |
| 2017/0172724 A1 | 6/2017 | Cartledge et al. | |
| 2017/0181751 A1 | 6/2017 | Larsen et al. | |
| 2017/0281382 A1 | 10/2017 | Lostetter et al. | |
| 2017/0367859 A1 | 12/2017 | Bloss et al. | |
| 2018/0036113 A1 | 2/2018 | Burkart et al. | |

(56) References Cited

U.S. PATENT DOCUMENTS

| | | |
|---|---|---|
| 2018/0071123 A1 | 3/2018 | Arbefeuille et al. |
| 2018/0071126 A1 | 3/2018 | Beard et al. |
| 2019/0321207 A1 | 10/2019 | Arbefeuille et al. |
| 2019/0388256 A1 | 12/2019 | Chung et al. |
| 2021/0169669 A1 | 6/2021 | Cato et al. |
| 2022/0151762 A1 | 5/2022 | Burkart et al. |
| 2022/0211525 A1 | 7/2022 | Bloss et al. |
| 2022/0395386 A1 | 12/2022 | Beard et al. |
| 2024/0390132 A1 | 11/2024 | Burkart et al. |

FOREIGN PATENT DOCUMENTS

| | | |
|---|---|---|
| CN | 102413794 A | 4/2012 |
| CN | 103347467 A | 10/2013 |
| CN | 103930075 A | 7/2014 |
| CN | 103945798 A | 7/2014 |
| CN | 106102596 A | 11/2016 |
| CN | 106344208 A | 1/2017 |
| EP | 0664107 A1 | 7/1995 |
| EP | 0679372 A2 | 11/1995 |
| EP | 1441668 B1 | 1/2008 |
| EP | 1915113 B1 | 3/2010 |
| EP | 1358903 B1 | 11/2011 |
| EP | 2481381 A1 | 8/2012 |
| EP | 1474074 B1 | 4/2014 |
| EP | 2749251 B1 | 7/2016 |
| EP | 3064173 A1 | 9/2016 |
| EP | 2956198 B1 | 11/2017 |
| EP | 3278771 A1 | 2/2018 |
| FR | 2896405 A1 | 7/2007 |
| GB | 1355373 A | 6/1974 |
| GB | 1506432 A | 4/1978 |
| GB | 2344054 A | 5/2000 |
| GB | 2448520 A | 10/2008 |
| JP | 08-126704 A | 5/1996 |
| JP | 09-309054 A | 12/1997 |
| JP | 2001-506902 A | 5/2001 |
| JP | 2002-503114 A | 1/2002 |
| JP | 2002-518086 A | 6/2002 |
| JP | 2003-502107 A | 1/2003 |
| JP | 2004-167239 A | 6/2004 |
| JP | 2004-188219 A | 7/2004 |
| JP | 2007-518465 A | 7/2007 |
| JP | 2011-511663 A | 4/2011 |
| JP | 2011-511693 A | 4/2011 |
| JP | 2011-516202 A | 5/2011 |
| JP | 2014-501563 A | 1/2014 |
| JP | 2014-501565 A | 1/2014 |
| JP | 2014-502180 A | 1/2014 |
| JP | 2014-533189 A | 12/2014 |
| WO | 96/18361 A1 | 6/1996 |
| WO | 97/48350 A1 | 12/1997 |
| WO | 98/27894 A1 | 7/1998 |
| WO | 99/65420 A1 | 12/1999 |
| WO | 00/13613 A1 | 3/2000 |
| WO | 01/21109 A1 | 3/2001 |
| WO | 02/28317 A2 | 4/2002 |
| WO | 03/34948 A1 | 5/2003 |
| WO | 2003/101518 A1 | 12/2003 |
| WO | 2005/070336 A1 | 8/2005 |
| WO | 2005/072652 A1 | 8/2005 |
| WO | 2006/007389 A1 | 1/2006 |
| WO | 2007/092354 A2 | 8/2007 |
| WO | 2008/047092 A1 | 4/2008 |
| WO | 2008/063464 A2 | 5/2008 |
| WO | 2009/102441 A1 | 8/2009 |
| WO | 2009/126227 A2 | 10/2009 |
| WO | 2009/148594 A1 | 12/2009 |
| WO | 2010/001012 A1 | 1/2010 |
| WO | 2010/024881 A1 | 3/2010 |
| WO | 2010/041038 A1 | 4/2010 |
| WO | 2010/044854 A1 | 4/2010 |
| WO | 2010/063795 A1 | 6/2010 |
| WO | 2010/081041 A1 | 7/2010 |
| WO | 2010/090699 A1 | 8/2010 |
| WO | 2010/105195 A2 | 9/2010 |
| WO | 2011/031981 A1 | 3/2011 |
| WO | 2011/062858 A1 | 5/2011 |
| WO | 2012/065080 A2 | 5/2012 |
| WO | 2012/068257 A2 | 5/2012 |
| WO | 2012/065080 A3 | 7/2012 |
| WO | 2012/136984 A1 | 10/2012 |
| WO | 2012/174254 A1 | 12/2012 |
| WO | 2013/040431 A1 | 3/2013 |
| WO | 2013/074266 A1 | 5/2013 |
| WO | 2013/137977 A1 | 9/2013 |
| WO | 2015/132668 A1 | 9/2015 |
| WO | 2018/005779 A1 | 1/2018 |
| WO | 2018/165358 A1 | 9/2018 |

OTHER PUBLICATIONS

Hsu et al, The Impact of Bird-Beak Configuration on Aortic Remodeling of Distal Arch Pathology After Thoracic Endovascular Aortic Repair with the Zenith Pro-Form TX2 Thoracic Endograft, Journal of Vascular Surgery, 2013, pp. 1-9.

Thread. (n.d) American Heritage (r) Dictionary of the English Language, Fifth Edition. (2011). Retrieved Feb. 14, 2016 from http://www.thefreedictionary.com/thread.

Ueda, et al., Incomplete Endograft Apposition to the Aortic Arch: Bird-Beak Configuration Increases Risk of Endoleak Formation after Thoracic Endovascular Aortic Repair, Radiology: vol. 255: No. 2; May 2010, pp. 645-652.

European Search Report for EP Patent Application No. 24162997.1, Issued on Jun. 19, 2024, 12 pages.

* cited by examiner

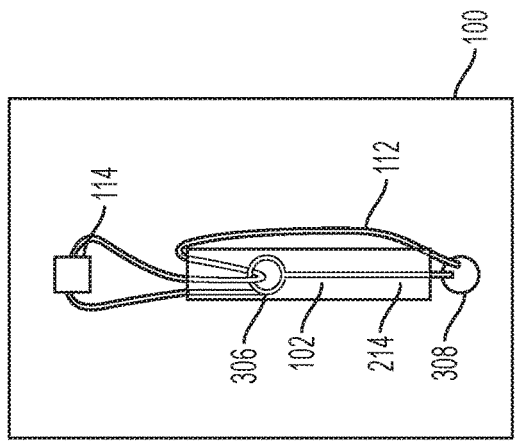
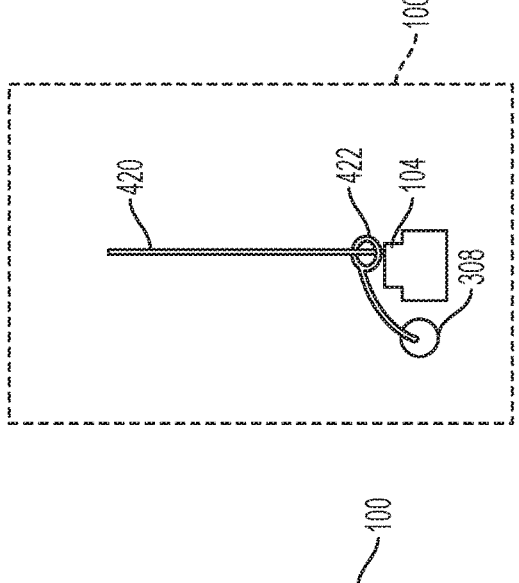
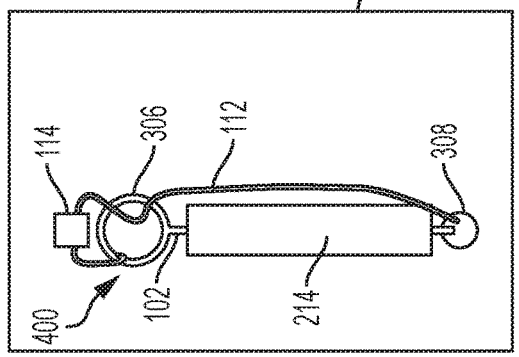
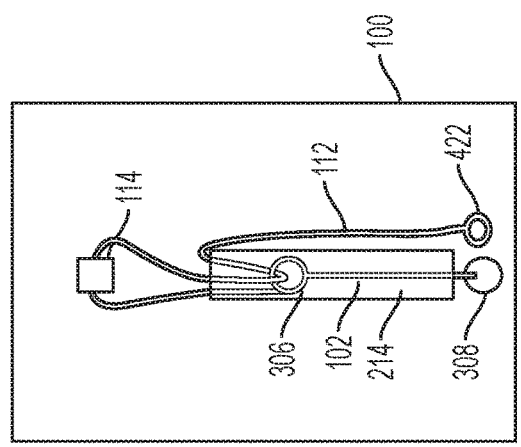
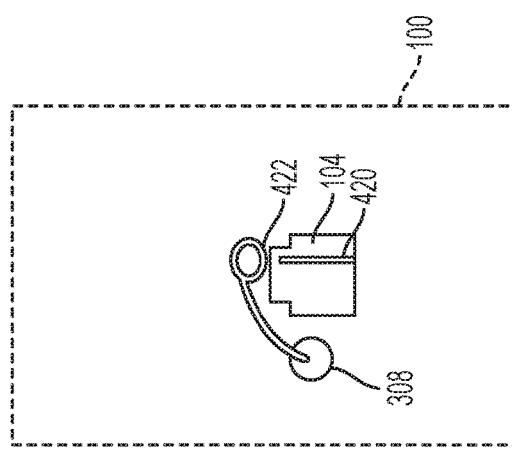

PIVOT DELIVERY SYSTEM FOR IMPLANTABLE MEDICAL DEVICE

CROSS-REFERENCE TO RELATED APPLICATION

This application is a national phase application of PCT Application No. PCT/US2018/049057, internationally filed on Aug. 31, 2018, which is herein incorporated by reference in its entirety for all purposes.

FIELD

The present invention relates to medical devices and methods for treating an anatomical space (e.g., vessels) of the body. More specifically, the invention relates to methods, apparatuses, and systems that include an implantable medical device prosthesis that allows for accurate deployment in the anatomical space.

BACKGROUND

Disease of the vasculature is increasingly common. Treatment of the vasculature may be difficult because of the tortuous nature and complexity of the vasculature. Aortic dissections, for example, commonly begin at or near the aortic valve root and continue to the ascending aorta and the aortic arch, and may also affect the upper part of the descending aorta. Medical devices implanted at a diseased state may be used for treatment of aortic dissections, aneurysms, and other diseases of the vasculature or other luminal systems of the body, such as the biliary tract, gastrointestinal tract, or respiratory system, for example.

It remains desirable to provide medical devices, systems and methods for repairing disease along the aorta and also for repairing disease along branches extending therefrom.

SUMMARY

According to one example ("Example 1"), a system for steering an implantable medical device includes an actuation line; a pivot coupled to the implantable medical device; and a tether attached at one end to the actuation line and arranged through the pivot and configured to orient the implantable medical device in response to tension applied to the actuation line and release from the pivot after the implantable medical device is oriented.

According to another example ("Example 2"), further to the system of Example 1, the pivot includes a loop attached to an exterior surface of the implantable medical device.

According to another example ("Example 3"), further to the system of Example 2, the loop includes a layer of graft material that forms a lumen between the exterior surface of the implantable medical device and the graft material.

According to another example ("Example 4"), further to the system of Example 3, the actuation line includes an eyelet and the tether is attached to the eyelet at the one end and arranged through the pivot and the eyelet.

According to another example ("Example 5"), further to the system of Example 4, the tether is arranged through the eyelet, arranged through the loop, and subsequently attached to the eyelet.

According to another example ("Example 6"), further to the system of any one of Examples 1-5, the pivot and the actuation line are configured to form a pulley to orient the implantable medical device in response to tension applied to the actuation line.

According to another example ("Example 7"), further to the system of any one of Examples 1-6, the system also includes an actuation line lumen and the tether is pulled into the actuation line lumen in response to tension applied to the actuation line.

According to another example ("Example 8"), further to the system of Example 7, the actuation line lumen is attached to the exterior surface of the implantable medical device proximal to the pivot.

According to another example ("Example 9"), further to the system of any one of Examples 7-8, the pivot and the actuation line lumen are configured to form the pulley to orient the implantable medical device in response to tension applied to the actuation line.

According to another example ("Example 10"), further to the system of any one of Examples 1-9, further comprising a removable lock wire configured to maintain coupling of the tether to the implantable medical device.

According to another example ("Example 11"), further to the system of Example 10, the tether includes an eyelet and the removable lock wire is arranged through the eyelet to couple the removable lock wire to the tether.

According to another example ("Example 12"), further to the system of Example 11, the eyelet of the tether is at or near a proximal end of the tether and a distal end of the tether is coupled to the actuation line.

According to another example ("Example 13"), further to the system of Example 12, the removable lock wire is arranged through a flow lumen of the implantable medical device and the tether is arranged from the flow lumen of the implantable medical device at the proximal end of the tether to an exterior surface of the removable lock wire at the distal end of the tether.

According to another example ("Example 14"), further to the system of Example 13, the tether is configured to release from the actuation line in response to withdraw of the removable lock wire from the eyelet of the tether.

According to another example ("Example 15"), further to the system of Example 10, the system also includes a catheter arranged through a lumen of the implantable medical device, wherein a proximal end of the tether is releasably coupled to the catheter, and a distal end of the tether is coupled to the actuation line.

According to an example ("Example 16") a delivery system includes a catheter; an implantable medical device arranged near a leading end of the catheter and including a proximal end, a distal end, and a flow lumen extending therebetween; a loop coupled to an exterior surface of the implantable medical device; a lumen coupled to the exterior surface of the implantable medical device proximal to the loop; an actuation line arranged through the lumen; and a tether coupled to the actuation line and arranged through the loop and configured to steer the implantable medical device in response to tension applied to the actuation line.

According to another example ("Example 17"), further to the system of Example 16, the loop and the lumen are pivot points and are configured to form a pulley between the tether and the actuation line to steer the implantable medical device in response to tension applied to the actuation line.

According to another example ("Example 18"), further to the system of Example 16, the system also includes a removable lock wire configured to maintain coupling of the tether to the implantable medical device, and wherein the tether is configured to release from the actuation line in response to withdraw of the removable lock wire.

According to another example ("Example 19"), a method of steering an implantable medical device includes delivering the implantable medical device to a target location within a patient's vasculature; and manipulating an actuation line, coupled to the implantable medical device by a tether arranged through a loop coupled to an exterior surface of the implantable medical device, to steer the implantable medical device.

According to another example ("Example 20"), further to the method of Example 19, the method also includes maintaining coupling of the tether to the implantable medical device by a removable lock wire, and wherein releasing the tether from the loop in response to withdraw of the removable lock wire.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 4A shows an illustration of an exterior view of another example delivery system in an unsteered configuration in accordance with an embodiment.

FIG. 4B shows an illustration of an interior view of the delivery system, shown in FIG. 4A, in accordance with an embodiment.

FIG. 4C shows an illustration of an exterior view of the delivery system, shown in FIGS. 4A-4B, in a steered configuration in accordance with an embodiment.

FIG. 4D shows an illustration of an interior view of the delivery system, shown in FIGS. 4A-C, in a configuration for removal of the tether in accordance with an embodiment.

FIG. 4E shows an illustration of an exterior view of the delivery system, shown in FIGS. 4A-4D, in a configuration for removal of the tether in accordance with an embodiment.

DETAILED DESCRIPTION

Figure 1:
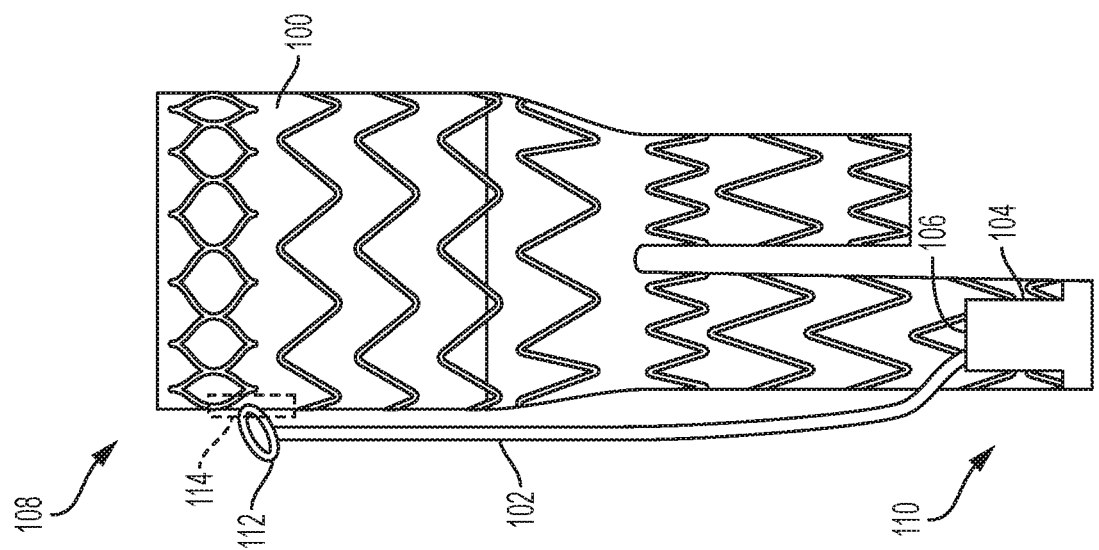
FIG. 1 shows an implantable medical device and an actuation line in accordance with an embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward apparatuses, systems, and methods that include an implantable medical device that may be used in treatment of the vasculature. The implantable medical device is delivered to the vasculature using a delivery system. In addition, the implantable medical devices described herein may be substantially cylindrical, include a bifurcation, or any combination of fenestrations. Further, the implantable medical devices may be configured to conform to the vasculature into which the implantable medical device is implanted, low-profile in order to enable delivery thereof using a minimally invasive procedure (e.g., transcatheter), and withstand forces and other stresses that occur once implanted in the vasculature.

The delivery system may be configured to position and/or steer the implantable medical device for accurate placement in the vasculature. To position and or steer the implantable medical device, the delivery system may include an actuation line (e.g., a wire, tether, or other member) that changes the position of the implantable medical device in response to a user applying force to the actuation line. The actuation line may be releasably coupled to the implantable medical device to avoid trauma to the vasculature after the implantable medical device is delivered and positioned. As discussed in further detail below, a tether, coupled to the actuation line, may be used in combination with a pivot coupled to the implantable medical device to orient the implantable medical device in response to tension applied to the actuation line. In certain instances, the actuation line, pivot, and tether may form a pulley arrangement that facilitates orienting of the implantable medical device with a patient's tortuous anatomy.

FIG. 1 shows an implantable medical device 100 and an actuation line 102 in accordance with various aspects of the present disclosure. The implantable medical device 100 is releasably coupled to a delivery system for delivery of the implantable medical device 100 to a target location within a patient's vasculature. The delivery system may include a catheter 104 that includes a leading end 106 and a trailing end (not shown in FIG. 1). The implantable medical device 100 may be arranged near the leading end 106 of the catheter 104. The catheter 104 may extend through a lumen of the implantable medical device 100 toward and past a proximal end 108 of the implantable medical device 100. The catheter 104 may also include a tip (not shown) at the leading end 106. As shown in FIG. 1, the implantable medical device 100 includes stent and graft components.

The implantable medical device 100 includes a proximal end 108, a distal end 110, and a flow lumen extending therebetween. The proximal end 108 of the implantable medical device 100 may be considered the end of the implantable medical device 100 that is closest to the target location within the patient's vasculature. The actuation line 102 may be coupled to the implantable medical device 100 at one or more locations. As shown in FIG. 1, the actuation line 102 is attached adjacent to or near the proximal end 108 of the implantable medical device 100 and accessible to a user of the delivery system. The actuation line 102 may be attached to other portions of the implantable medical device 100.

As shown, the actuation line 102 is coupled to the implantable medical device 100 via at least one tether 112. The tether 112 may be arranged through a portion of the implantable medical device 100 and through the actuation line 102 to couple the line 102 to the implantable medical device 100. In certain instances, and as shown in FIG. 1, the at least one tether 112 is arranged through the implantable medical device 100 near or adjacent to the proximal end 108 of the implantable medical device 100. The at least one tether 112 may be a single tether, as shown in FIG. 1. In other instances, the implantable medical device 100 may include a loop 114 attached or coupled to an exterior surface of the implantable medical device 100. The loop 114 may include a layer of graft material that forms a lumen between the exterior surface of the implantable medical device 100 and the graft material. The tether 112 may be arranged through the loop 114 to couple the line 102 to the implantable medical device 100. In other instances, the loop 114 or pivot may be a hole or holes through graft material of the implantable medical device 100. In these instances, the tether 112 is arranged through the hole or holes of implantable medical device 100.

In certain instances, the line 102 is an actuation line 102 configured to steer/orient the implantable medical device 100 during delivery thereof. The actuation line 102 may include a stiffness such that a user operating the delivery system may apply force to the actuation line 102 and bidirectionally steer (e.g., proximally and distally relative to the target location within the patient's vasculature) the implantable medical device 100. For example, the actuation line 102 may have a stiffness that is greater than a stiffness of the tether 112. The stiffness of the actuation line 102 and/or the location to which the actuation line 102 is coupled to the implantable medical device 100 may facilitate deploying and arranging the implantable medical device 100 relative to the target location within the patient's vasculature. For example, the implantable medical device 100 may be configured to deploy at a tortuous vessel having a curvature with at least one inflection point. In certain instances, the actuation line 102 is configured to maintain the proximal end 108 of the implantable medical device 100 approximately perpendicular to the inflection point in the curvature of the tortuous vessel during delivery of the implantable medical device 100.

The actuation line 102 may be uncoupled or released from the implantable medical device 100 subsequent to the implantable medical device 100 being positioned and deployed at the target location within the patient's vasculature and removed from the patient. The actuation line 102 can include an eyelet or opening in a leading end through which the tether 112 is arranged. In addition, the tether 112 may be attached to the actuation line 102 at the eyelet or at another location as explained in further detail below. In other instances, the tether 112 is configured to be removed or unthreaded to uncouple the actuation line 102 from the implantable medical device 100.

Figure 2:
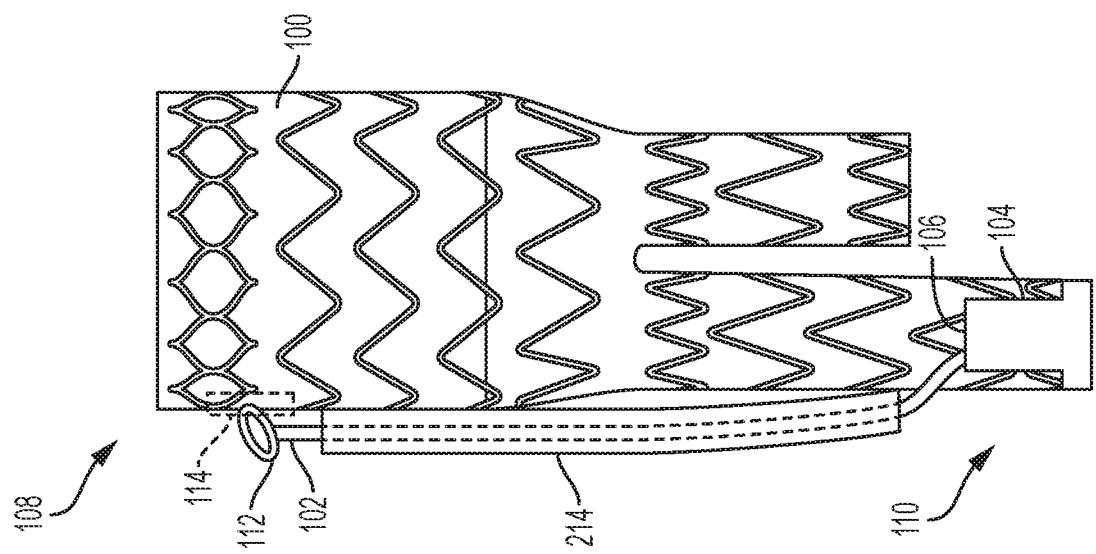
FIG. 2 shows another implantable medical device and an actuation line in accordance with an embodiment.

FIG. 2 shows another implantable medical device 100 and an actuation line 102 in accordance with various aspects of the present disclosure. The implantable medical device 100 may be releasably coupled to a delivery system. The delivery system may include a catheter 104 that includes a leading end 106 and a trailing end (not shown in FIG. 2). The implantable medical device 100 may be arranged near the leading end 106 of the catheter 104. The delivery system may be configured to deliver the implantable medical device 100 to a target location within a patient's vasculature. In certain instances, the implantable medical device 100 may be configured to deploy at a tortuous vessel having a curvature with at least one inflection point. To facilitate deploying of the implantable medical device 100, the delivery system may include the actuation line 102 configured to maintain a proximal end 108 (or distal end 110) of the implantable medical device 100 approximately perpendicular to the inflection point in the curvature of the tortuous vessel during delivery of the implantable medical device 100.

The actuation line 102 (accessible to a user of the delivery system), for example, is configured to steer/orient the implantable medical device 100 during delivery thereof, and is releasably coupled to the implantable medical device 100 via at least one tether 112. The tether 112 may be arranged through a portion of the implantable medical device 100 and through the actuation line 102 to couple the actuation line 102 to the implantable medical device 100. In certain instances, and as shown in FIG. 2, the at least one tether 112 is arranged through the implantable medical device 100 near or adjacent to the proximal end 108 of the implantable medical device 100. In other instances, the implantable medical device 100 may include a loop 114 attached or coupled to an exterior surface of the implantable medical device 100. The loop 114 may include a layer of graft material that forms a lumen between the exterior surface of the implantable medical device 100 and the graft material. The tether 112 may be arranged through the loop 114 to couple the line 102 to the implantable medical device 100. In other instances, the loop 114 or pivot may be a hole or holes through graft material of the implantable medical device 100. In these instances, the tether 112 is arranged through the hole or holes of implantable medical device 100.

In addition, the actuation line 102 may be arranged through a sleeve 214 that is attached to an exterior portion of the implantable medical device 100. The implantable medical device 100 may include a graft component and one or more stent components. The sleeve 214 may be formed of a similar material or the same material as the graft component of the implantable medical device 100. The sleeve 214 may include a lumen through which the actuation line 102 is arranged. In certain instances, the sleeve 214 is an enclosed structure which forms the lumen, or the sleeve 214 is a layer of graft material that forms a lumen between the sleeve 214 and the implantable medical device 100. The sleeve 214 may facilitate the actuation line 102 steering the implantable medical device 100. The sleeve 214 may prevent traumatic interaction between the actuation line 102 and a vessel wall. In addition, the sleeve 214 may enhance the connection between the actuation line 102 and the implantable medical device 100 when a user applies force or tension to the actuation line 102. As shown, the sleeve 214 has a length similar to the length of the implantable medical device 100. In other instances, the sleeve 214 may have a shorter length than the implantable medical device 100 or a longer length than the implantable medical device.

The actuation line 102 may include a stiffness such that a user operating the delivery system may apply force to the actuation line 102 and bidirectionally steer (e.g., proximally and distally relative to the target location within the patient's vasculature) the implantable medical device 100. For example, the actuation line 102 may have a stiffness that is greater than a stiffness of the tether 112. The stiffness of the actuation line 102 and/or the location to which the actuation line 102 is coupled to the implantable medical device 100 may facilitate deploying and arranging the implantable medical device 100 relative to the target location within the patient's vasculature.

Figure 3A:
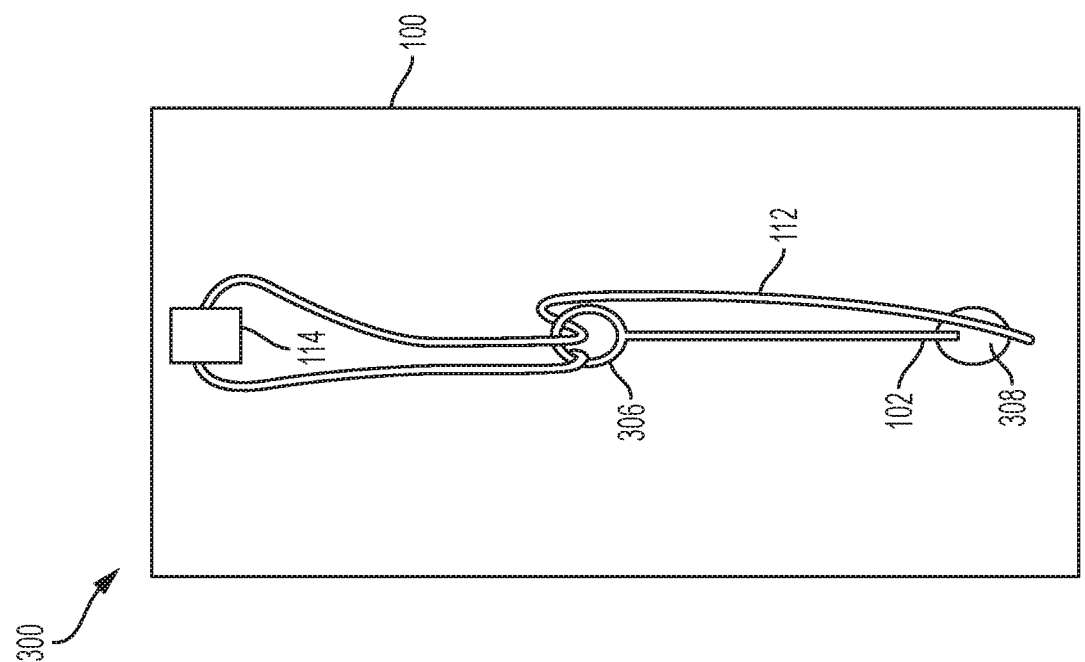
FIG. 3A shows an illustration of an exterior view of an example delivery system in an unsteered configuration in accordance with an embodiment.

FIG. 3A shows an illustration of an exterior view of an example delivery system 300 in an unsteered configuration in accordance with an embodiment. The delivery system 300 may be used for steering an implantable medical device 100

Figure 3B:
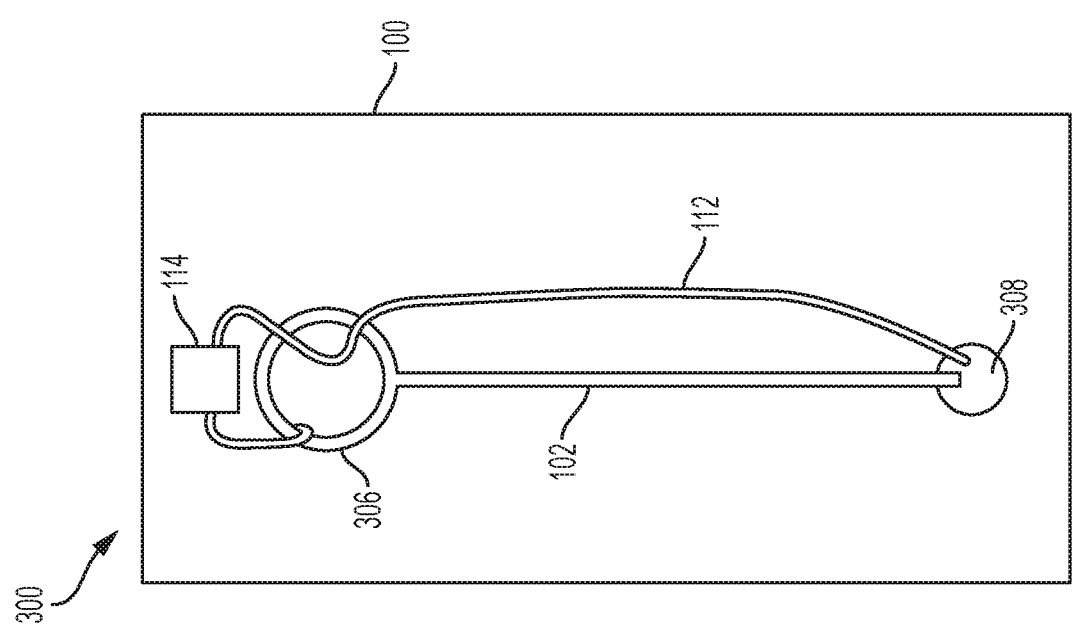
FIG. 3B shows an illustration of an exterior view of the delivery system, shown in FIG. 3A, in a steered configuration in accordance with an embodiment.

(e.g., as shown in FIGS. 1-2). The delivery system 300 may include an actuation line 102. As shown in FIGS. 3A-B, the actuation line 102 includes an eyelet 306. In addition, the delivery system 300 also includes a pivot 114 and a tether 112. For ease of illustration, element 308 is illustrative of a hole in the implantable medical device 100. As FIGS. 3A-B are an illustration from an exterior view of the implantable medical device 100, the element 308 indicates a pathway from an exterior surface of the implantable medical device 100 to an interior (flow lumen) of the implantable medical device 100.

Consistent with the loop shown in FIGS. 1-2, the pivot 114 may be coupled to the implantable medical device 100. In addition, and as shown in FIGS. 1-2, the pivot 114 may also be attached to an exterior surface of the implantable medical device 100. In certain instances, the pivot 114 may be a hole or holes in the implantable medical device 100. In other instances, the pivot 114 is a loop that includes a layer of graft material that forms a lumen between the exterior surface of the implantable medical device 100 and the graft material.

As shown in FIGS. 3A-B, the tether 112 may be arranged through the loop 114 to couple the actuation line 102 to the implantable medical device 100. In addition, one end of the tether 112 may be attached to the actuation line 102. In certain instances, the tether 112 may be attached to the actuation line 102 at the eyelet 306. From the attachment at the eyelet 306 (or another distal end portion of the actuation line 102), the tether 112 is arranged through the pivot 114. In addition, after being arranged through the pivot 114 (or loop), the tether 112 travels proximally (e.g., toward a user along an exterior surface of the implantable medical device 100).

In certain instances, each of the tether 112 and the actuation line 102 may transition between the exterior surface of the implantable medical device 100 to an interior (flow lumen) of the implantable medical device 100 at element 308. At this point, the tether 112 and the actuation line 102 may enter a catheter (e.g., as shown in FIGS. 1-2) at which the implantable medical device 100 may be arranged for delivery. The tether 112 and/or the actuation line 102 can travel proximally toward a user or a handle portion of the delivery system 300. In this manner, a user may apply tension to the tether 112 and/or the actuation line 102. FIG. 3B shows an example illustration of the delivery system 300 in a steering configuration (e.g., when a user has applied tension to the actuation line 102. As shown in FIG. 3B, the actuation line 102 has been withdrawn proximally relative to the position in the unsteered configuration shown in FIG. 3A.

Figure 7A:
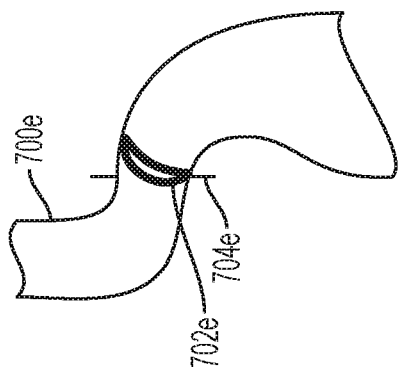
FIGS. 7A-7E show side view illustrations of expandable device angulation relative to a target location in accordance with various aspects of the present disclosure.

The tether 112, by way of attachment or coupling to the actuation line 102, is pulled or drawn proximally along with the actuation line 102 when tension is applied to the actuation line 102. As a result of the tether 112 being arranged through the pivot 114, the tether 112 will curve, orient, or actuate the implantable medical device 100. The pivot 114 being coupled or attached to the implantable medical device 100 and the tether 112 being arranged through the pivot 114 pulls, curves, orients, or forces a configuration change to an end of the implantable medical device 100 to which the pivot 114 is coupled. As shown in FIG. 7A, the actuation line 102, tether 112, and pivot 114 may, in combination, angle or curve a leading end of the device in tortuous anatomy to orient the implantable medical device 100.

In certain instances, the pivot 114 and the actuation line 102 are configured to form a pulley to orient the implantable medical device 100 in response to tension applied to the actuation line 102. The tether 112 may loop around the pivot 114 to form a pulley when the actuation line 102 is tensioned or pulled proximally.

FIG. 4A shows an illustration of an exterior view of another example delivery system 400 in an unsteered configuration in accordance with an embodiment. The delivery system 400 may be used for steering an implantable medical device 100 (e.g., as shown in FIGS. 1-2). The delivery 400 may include an actuation line 102 and an actuation line sleeve 214. The actuation line sleeve 214 may be attached or coupled to an exterior surface of the implantable medical device 100. In addition, the actuation line sleeve 214 may facilitate the actuation line 102 steering the implantable medical device 100. The actuation line sleeve 214 may prevent traumatic interaction between the actuation line 102 and a vessel wall (and may form a part of a pulley as discussed in further detail below). In addition, the actuation line sleeve 214 may enhance the connection between the actuation line 102 and the implantable medical device 100 when a user applies force or tension to the actuation line 102. The delivery system 400 may also include a pivot or loop 114 coupled to the implantable medical device. The loop 114 may include a layer of loop material that forms a lumen between the exterior surface of the implantable medical device 100 defined by a graft material. The tether 112 may be arranged through the loop 114 and external to the actuation line sleeve 214.

As shown in FIG. 4A, the actuation line 102 includes an eyelet 306. One end of the tether 112 may be attached to the actuation line 102. In certain instances, the tether 112 may be attached to the actuation line 102 at the eyelet 306. From the attachment at the eyelet 306 (or another distal end portion of the actuation line 102), the tether 112 is arranged through the loop 114. In addition, after being arranged through the loop 114 (or pivot), the tether 112 travels proximally (e.g., toward a user along an exterior surface of the implantable medical device 100). As shown in FIG. 4A, the tether 112 is arranged through the eyelet 306, arranged through the loop 114, and subsequently attached to the eyelet 306 (e.g., as the tether 112 approaches a leading or distal end of the implantable medical device 100).

In certain instances, each of the tether 112 and the actuation line 102 may transition between the exterior surface of the implantable medical device 100 to an interior (flow lumen) of the implantable medical device 100 at element 308. For ease of illustration, element 308 is illustrative of a hole in the implantable medical device 100. FIG. 4A is an illustration from an exterior view of the implantable medical device 100 whereas FIG. 4B is an illustration from an interior view of the implantable medical device 100 with the element 308 indicates a pathway from an exterior surface of the implantable medical device 100 to an interior (flow lumen) of the implantable medical device 100.

As shown in FIG. 4B, the delivery system 400 may include a removable lock wire 420. The removable lock wire 420, in certain instances, is configured to maintain coupling of the tether 112 to the implantable medical device 100. In addition, the tether 112 is configured to release from the actuation line 102 in response to withdrawal of the removable lock wire 420 as shown in FIGS. 4D-E and explained in further detail below. In certain instances, the removable lock wire 420 may be attached to the tether 112. In other instances, and as shown in FIG. 4B, the removable lock wire 420 may be arranged through a portion of the tether 112. The tether 112, for example, may include an eyelet 422 arranged at an end of the tether 112. In instances where the tether 112 includes an eyelet 422, the removeable lock wire 420 is arranged through the eyelet 422 of the tether 112 to couple the removable lock wire 420 to the tether 112.

The eyelet 422 of the tether 112 may be arranged at one end of the tether 112 with the other end of the tether 112 being attached to the eyelet 306 of the actuation line 102. In certain instances, the eyelet 422 of the tether 112 is at or near a proximal end of the tether 112 and a distal end of the tether 112 is coupled to the actuation line 102.

As shown in FIG. 4B, the removable lock wire 420 is arranged through a flow lumen of the implantable medical device 100 and the tether 112 is arranged from the flow lumen (e.g., interior portion) of the implantable medical device 100 at the proximal end of the tether 112 to an exterior surface of the removable lock wire 420 at the distal end of the tether.

As also shown in FIG. 4B, the delivery system 400 may include a catheter 104 with the implantable medical device 100 arranged near a leading end of the catheter 104 (as shown in further detail in FIGS. 1-2). The catheter 104 may extend through a lumen of the implantable medical device 100 toward and past a leading end of the implantable medical device 100. The catheter 104 may also include a tip (not shown) at the leading end. The removable lock wire 420 may be arranged through a lumen of the catheter 104, and may be withdrawn into the lumen of the catheter 104, as shown in FIG. 4D, to release the tether 112.

FIG. 4C shows an illustration of an exterior view the delivery system 400, shown in FIGS. 4A-B, in a steered configuration in accordance with an embodiment. The tether 112, by way of attachment or coupling to the actuation line 102, is pulled or drawn proximally along with the actuation line 102 when tension is applied to the actuation line 102. As a result of the tether 112 being arranged through the loop 114, the tether 112 will curve, orient, or actuate the implantable medical device 100. The loop 114 being coupled or attached to the implantable medical device 100 and the tether 112 being arranged through the loop 114 pulls, curves, orients, or forces a configuration change to an end of the implantable medical device 100 to which the loop 114 is coupled. As shown in FIG. 7A, the actuation line 102, tether 112, and loop 114 may, in combination, angle or curve a leading end of the device in tortuous anatomy to orient the implantable medical device 100.

In addition, the tether 112 is pulled into a lumen defined by the actuation line sleeve 214 in response to tension applied to the actuation line 102. In certain instances, the tether 112 may follow a pathway that begins from the tether 112 attachment at the eyelet 306 of the actuation line 102, the tether 112 loops through the loop 114 back into the lumen defined by the actuation line sleeve 214, through the eyelet 306 of the actuation line 102, and back out of the lumen defined by the actuation line sleeve 214 as shown in FIG. 4C. The tether 112 (and actuation line 102) may then enter the implantable medical device 100 at element 308. At this point, the actuation line 102 may enter the catheter 104 and travel proximally toward a user or a handle portion of the delivery system 400. In this manner, a user may apply tension to the actuation line 102.

As shown in FIG. 4C, the actuation line sleeve 214 is attached to an exterior surface of the implantable medical device 100 proximal to the loop 114 (or pivot). In certain instances, the pathway shown in FIG. 4C forms a pulley arrangement for orienting the implantable medical device 100. For example, the loop 114 and the actuation line sleeve 214 are configured to form a pulley to orient the implantable medical device 100 in response to tension applied to the actuation line 102. The loop 114 and the actuation line sleeve 214 are pivot points in the pulley and are configured to form a pulley between the tether 112 and the actuation line 102 to steer the implantable medical device 100 in response to tension applied to the actuation line 102.

FIG. 4D shows an illustration of an interior view of the delivery system 400 in a configuration for removal of the tether 112. The tether 112 is configured to release from the actuation line 102 in response to withdrawal of the removable lock wire 420 from the eyelet 422 of the tether 112. As shown in FIG. 4D, the removable lock wire 420 may be withdrawn into the catheter 104. The removable lock wire 420 may be removed after the implantable medical device 100 is oriented in a desired configuration at a target location within a patient.

FIG. 4E shows an illustration of an exterior view of the delivery system 400 in a configuration for removal of the tether in accordance with an embodiment. The tether 112 is configured to release from the actuation line 102 in response to withdraw of the removable lock wire 420. Continued tension applied to the actuation line 102 after release or removal of the removable lock wire 420 pulls the tether 112 through element 308 (e.g., a hole in the implantable medical device 100). At this point, the tether 112 and the actuation line 102 are uncoupled from the medical device 100. In addition, a user may continue to apply tension or withdraw the actuation line 102 to remove the actuation line 102 and the tether 112, attached to the actuation line 102, from the patient.

Figure 5:
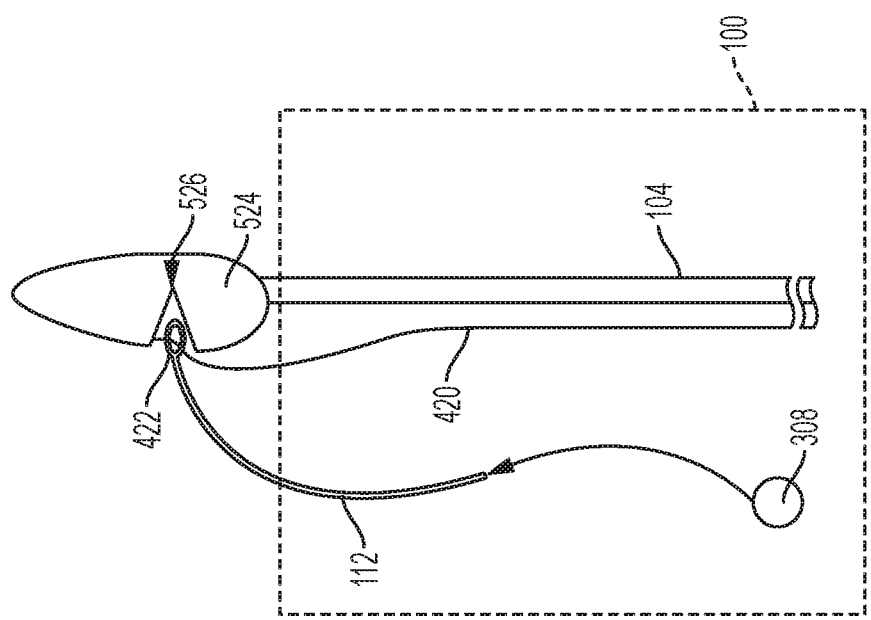
FIG. 5 shows an illustration of an interior view of an implantable device with an example lock wire arrangement in accordance with an embodiment.

FIG. 5 shows an illustration of an interior view of an implantable device 100 with an example lock wire 420 arrangement in accordance with an embodiment. A catheter 104 is also shown in FIG. 5, the catheter 104 is arranged through a flow lumen of the implantable medical device 100. At a distal end of the catheter 104 is an olive 524. The olive 524 may be an atraumatic tip of the catheter 104 and delivery system.

In certain instances, a lock wire 420, as discussed in further detail above with reference to FIGS. 4A-E, may be embedded in a portion of the olive 524. The olive 524 may include a cut-away section 526 as shown in FIG. 5. In certain instances, the lock wire 420 is embedded in the cut-away section 526 of the olive 524 during delivering and steering/orienting of the implantable medical device 100. The lock wire 420 may be arranged through an eyelet 422 of a tether 112 for steering/orienting of the implantable medical device 100 as discussed in detail above. An end of the tether 112 that includes the eyelet 422 is coupled to the catheter 104 by way of the lock wire 420 with another end of the tether 112 being external to the implantable medical device 100 for attachment or coupling to an actuation line 102 (not shown). As shown in FIG. 5, the tether 112 transitions from an interior of the implantable medical device 100 to an exterior by being arranged through element 308 (e.g., a hole in the implantable medical device 100).

The catheter 104 shown in FIG. 5 is provided as an example of the various features of the catheter 104 and, although the combination of those illustrated features is clearly within the scope of invention, that example and its illustration is not meant to suggest the inventive concepts provided herein are limited from fewer features, additional features, or alternative features to one or more of those features shown in FIG. 5. For example, in various embodiments, the catheter 104 and/or lock wire 420 arrangement shown in FIG. 5 may be included in the delivery systems described with reference to FIGS. 1-4. The delivery systems, for example, may include an olive 524 or a lock wire 420 may be pinned to the olive 524. It should also be understood that the reverse is true as well. For example, the tether 112 and lock wire 420 shown in FIG. 5 may be employed in connection with the actuation line 102 shown in FIGS. 4A-E.

Figure 6B:
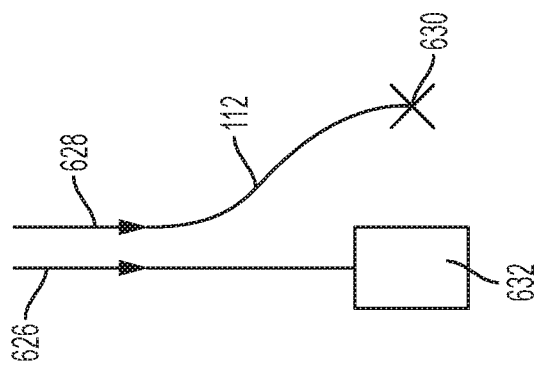
FIG. 6B shows an illustration of an interior view of the delivery system, shown in FIG. 6A, in accordance with an embodiment.
Figure 6A:
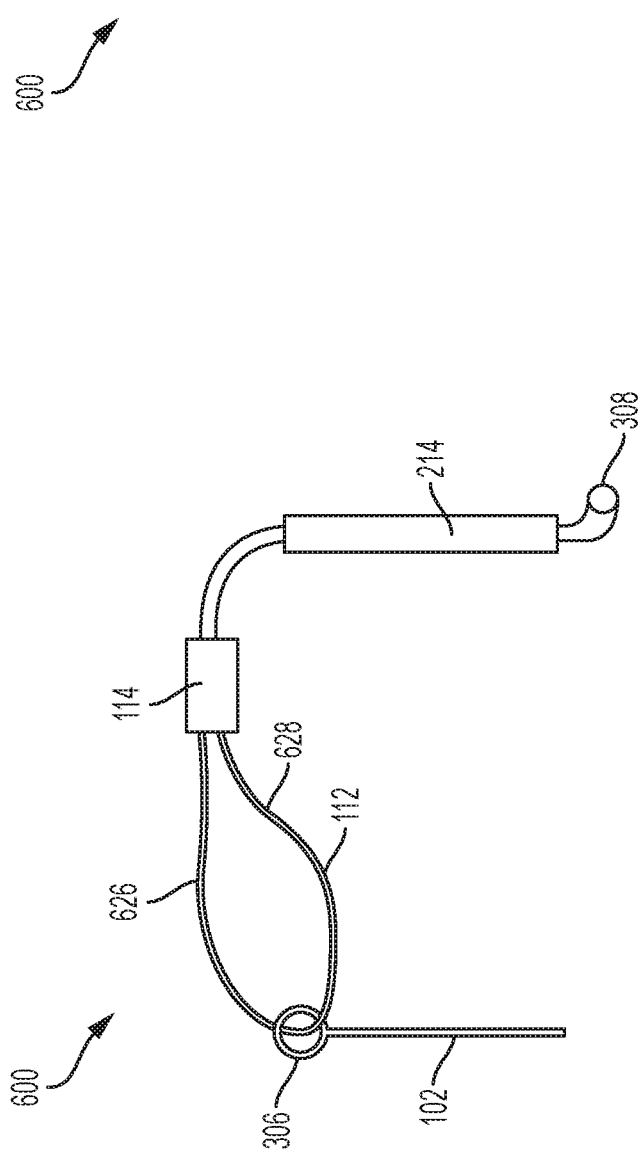
FIG. 6A shows an illustration of an exterior view of another example delivery system in accordance with an embodiment.

FIG. 6A shows an illustration of an exterior view of another example delivery system 600 in accordance with an embodiment. The delivery system 600 may be used for steering an implantable medical device (e.g., as shown in FIGS. 1-2). The delivery system 600 may include an actuation line 102 and a sleeve 214. The sleeve 214 may be attached or coupled to an exterior surface of the implantable medical device 100.

The delivery system 600 may also include a pivot or loop 114 coupled to the implantable medical device 100. The loop 114 may include a layer of loop material that forms a lumen between the exterior surface of the implantable medical device 100 and defined by a graft material. The tether 112 may be arranged through the loop 114 and external to the sleeve 214. As shown in FIG. 6A, the actuation line 102 includes an eyelet 306 with the tether 112 being routed through the eyelet 306. In addition, and as shown in FIG. 6A, the tether 112 includes two portions 626, 628 as a result of the looping through the eyelet 306 of the actuation line 102. The portions 626, 628 of the tether 112 are arranged through the lumen defined by the sleeve 214 and routed to an interior of the implantable medical device 100 through a hole in the implantable medical device 100 illustrated by element 308.

FIG. 6B shows an illustration of an interior view of the delivery system 600, shown in FIG. 6A, in accordance with an embodiment. One of the portions 626 of the tether 112 may be attached to a catheter as illustrated by element 630. In addition, the other of the portions 628 may be coupled to a portion of a delivery handle 632, accessible to a user. The user may apply tension to remove the portion of the delivery handle 632 to apply tension to the tether 112. The tether 112 may then be released from the attachment point 630 on the catheter and thereby decouple from the eyelet 306 of the actuation line 102. This decouples the actuation line 102 from the implantable medical device 100 after orientation is accomplished.

FIGS. 7A-E show side view illustrations of expandable device angulation relative to a target location 700*a-e* in accordance with various aspects of the present disclosure. Each of FIGS. 7A-E show a side profile of a leading (or proximal) end 700*a-e* of an expandable device, consistent with various aspects of the present disclosure. In certain instances, the target location 700*a-e* may be at a tortuous vessel of a patient. The target location 700*a-e* into which the expandable device is implanted may have angulation (e.g., a curvature with at least one inflection point 704*a-e*). The target location 700*a-e* may be an angulated abdominal aortic aneurism (AAA).

Figure 7B:
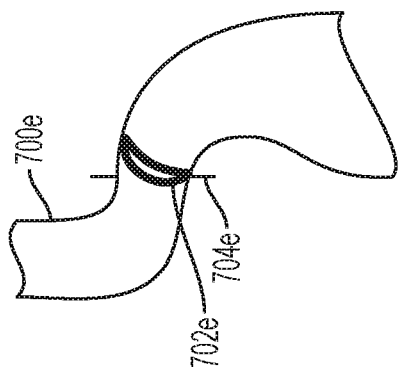
Figure 7C:
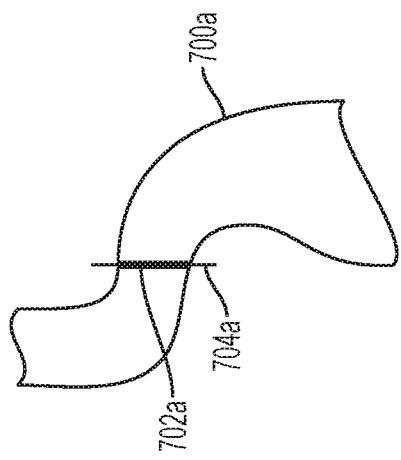
Figure 7D:
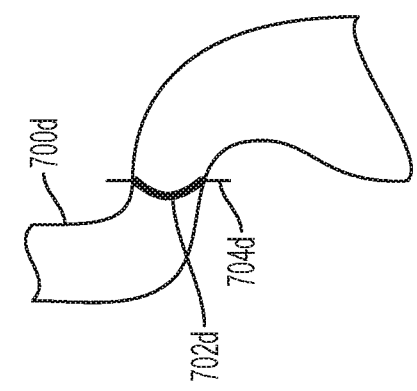
Figure 7E:
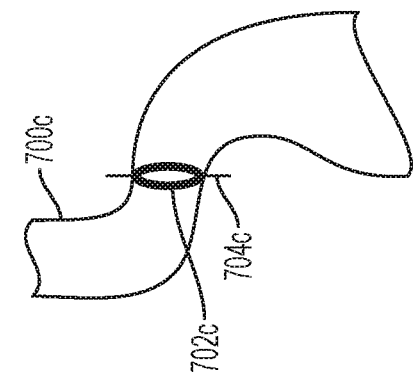

In certain instances, one of the ends 702*a-e* of the expandable device may be deployed perpendicular to the inflection point in the curvature of the tortuous vessel during delivery of the expandable device. Non-perpendicularity may negatively affect the ability of the expandable device to seal against the target location 700*a-e*. FIG. 7A shows the leading (or proximal) end 702*a* deployed perpendicular to the inflection point 704*a*. In certain instances, perpendicularity of the expandable device may be a function of device flatness, angulation, and rotational alignment. FIG. 7B shows the leading (or proximal) end 702*b* of an expandable device angled relative to the inflection point 704*b* of the target location 700*b*. FIG. 7C shows the leading (or proximal) end 702*c* of an expandable device rotated relative to the inflection point 704*c* of the target location 700*c*. FIG. 7D shows the leading (or proximal) end 702*d* of an expandable device deformed relative to the inflection point 704*d* of the target location 700*d*. FIG. 7E shows the leading (or proximal) end 702*e* of an expandable device deformed or flat, rotated, and angled relative to the inflection point 704*e* of the target location 700*e*.

Device deployment and performance can be enhanced by steering the device to an appropriate location while maintaining one of the ends of the expandable device perpendicular to the target location 700*a-e* (e.g., curvature of a vessel with at least one inflection point 704*a-e*) during and after deployment. The actuation lines and arrangements thereof discussed herein facilitate maintaining the expandable device perpendicular during and after deployment (as shown in FIG. 7A) and mitigate against non-perpendicular, angled, or flat deployment (as shown in FIGS. 7B-E).

The lines discussed herein may be formed from metallic, polymeric or natural materials such as stainless steels, cobalt-chromium alloys and nitinol. Further, actuation lines can also be formed from high strength polymer fibers such as ultra high molecular weight polyethylene fibers (e.g., Spectra™., Dyneema Purity™., etc.) or aramid fibers (e.g., Technora™, etc.). In certain instances, the actuation line may have a great column strength than the tethers.

The graft components may be made up of any material which is suitable for use as a graft in the chosen body lumen and being resistant to expansion as discussed herein. The graft components may be composed of the same or different materials. Furthermore, the graft components may include multiple layers of material that can be the same material or different material. In one embodiment, said materials can be used in combination and assembled together to comprise a graft. The graft materials used in a stent graft can be extruded, coated or formed from wrapped films, or a combination thereof. Polymers, biodegradable and natural materials can be used for specific applications.

Examples of synthetic polymers include, but are not limited to, nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, said graft is made from a class of polyesters such as polyethylene terephthalate including DACRON®. and MYLAR® and polyaramids such as KEVLAR®., polyfluorocarbons such as polytetrafluoroethylene (PTFE) with and without copolymerized hexafluoropropylene (TEFLON®. or GORE-TEX®.), and porous or nonporous polyurethanes. In another embodiment, said graft comprises expanded fluorocarbon polymers (especially PTFE) materials. Included in the class of preferred fluoropolymers are polytetrafluoroethylene (PTFE), fluorinated ethylene propylene (FEP), copolymers of tetrafluoroethylene (TFE) and perfluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is ePTFE. In another embodiment, said graft comprises a combination of said materials listed above. In another embodiment, said graft is substantially impermeable to bodily fluids. Said substantially impermeable graft can be made from materials that are substantially impermeable to bodily fluids or can be constructed from permeable materials treated or manufactured to be substantially impermeable to bodily fluids (e.g. by layering different types of materials described above or known in the art). In another embodiment, said outermost tube comprises ePTFE. In another embodiment, said innermost tube comprises ePTFE. In another embodiment, said innermost and outermost tube comprises ePTFE film that has been wrapped into a tube. In another embodiment, said secondary stent is covered with any of the material disclosed herein or known in the art. In another embodiment, the secondary stent covering comprises ePTFE.

Additional examples of graft materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (methyl vinyl ether), chlorotrifluoroethylene (CTFE), pentafluoropropene, trifluoroethylene, hexafluoroacetone, hexafluoroisobutylene, fluorinated poly(ethylene-co-propylene (FPEP), poly(hexafluoropropene) (PHFP), poly(chlorotrifluoroethylene) (PCTFE), poly(vinylidene fluoride) (PVDF), poly(vinylidene fluoride-co-tetrafluoroethylene) (PVDF-TFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PTFEP) poly(hexafluoropropene-co-vinyl alcohol) (PHFP-VAL), poly(ethylene-co-tetrafluoroethylene) (PETFE), poly(ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805, incorporated by reference herein in its entirety for all purposes. Additional polyfluorocopolymers include tetrafluoroethylene (TFE)/perfluoroalkylvinylether (PAVE). PAVE can be perfluoromethylvinylether (PMVE), perfluoroethylvinylether (PEVE), or perfluoropropylvinylether (PPVE), as described in U.S. Publication 2006/0198866 and U.S. Pat. No. 7,049,380, both of which are incorporated by reference herein for all purposes in their entireties. Other polymers and copolymers include, polylactide, polycaprolacton-glycolide, polyorthoesters, polyanhydrides; poly-aminoacids; polysaccharides; polyphosphazenes; poly(ether-ester) copolymers, e.g., PEO-PLLA, or blends thereof, polydimethyl-siolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters and any polymer and copolymers described in U.S. Publication 2004/0063805, incorporated by reference herein in its entity.

The graft components, as discussed herein, may be attached to the self-expanding stent elements by using a coupling member that is generally a flat ribbon or tape having at least one generally flat surface. In certain instances, the tape member is made from expanded PTFE (ePTFE) coated with an adhesive. The adhesive may be a thermoplastic adhesive. In certain instances, the thermoplastic adhesive may be fluorinated ethylene propylene (FEP). More specifically, an FEP-coated side of the ePTFE may face toward and contacts an exterior surface of the self-expanding stent and graft component, thus attaching the self-expanding stent to the graft component.

The stent component(s) discussed herein can be fabricated from a variety of biocompatible materials. These materials may include 316L stainless steel, cobalt-chromium-nickel-molybdenum-iron alloy ("cobalt-chromium"), other cobalt alloys such as L605, tantalum, Nitinol, or other biocompatible metals. In certain instances, as discussed in detail above, the stent (and graft) may be self-expanding. In other instances, the prosthesis may be balloon expandable.

The stent component(s) discussed herein may be constructed from a reasonably high strength material, i.e., one which is resistant to plastic deformation when stressed. In one embodiment, the stent component(s) comprise a wire which is helically wound around a mandrel having pins arranged thereon so that the helical turns and undulations can be formed simultaneously. Other constructions may also be used. In certain instances, the stent component(s) are made from a super-elastic alloy. There are a variety of disclosures in which super-elastic alloys such as nitinol are used in stents. See for example, U.S. Pat. No. 4,503,569, to Dotter; U.S. Pat. No. 4,512,338, to Balko et al.; U.S. Pat. No. 4,990,155, to Wilkoff; U.S. Pat. No. 5,037,427, to Harada, et al.; U.S. Pat. No. 5,147,370, to MacNamara et al.; U.S. Pat. No. 5,211,658, to Clouse; and U.S. Pat. No. 5,221,261, to Termin et al.

A variety of materials variously metallic, super elastic alloys, such as Nitinol, are suitable for use in the stent component(s). Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY®), platinum/tungsten alloys, and especially the nickel-titanium alloys generically known as "nitinol".

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device and a system for steering the implantable medical device, the system comprising:
   an actuation line;
   a pivot forming a loop coupled to an exterior surface of the implantable medical device; and
   a tether attached at one end to the actuation line and arranged through the loop of the pivot and configured to orient the implantable medical device in response to tension applied to the actuation line and release from the pivot after the implantable medical device is oriented.

2. The system of claim 1, wherein the loop comprises a layer of loop material that forms a lumen between the exterior surface of the implantable medical device defined by a graft material.

3. The system of claim 2, wherein the actuation line includes an eyelet and the tether is attached to the eyelet at the one end and arranged through the pivot and the eyelet.

4. The system of claim 3, wherein the tether is arranged through the eyelet, arranged through the loop, and subsequently attached to the eyelet.

5. The system of claim 1, wherein the pivot and the actuation line are configured to form a pulley to orient the implantable medical device in response to tension applied to the actuation line.

6. The system of claim 1, further comprising an actuation line sleeve and the tether is pulled into the actuation line sleeve in response to tension applied to the actuation line.

7. The system of claim 6, wherein the actuation line sleeve is attached to the exterior surface of the implantable medical device proximal to the pivot.

8. The system of claim 6, wherein the pivot and the actuation line sleeve are configured to form a pulley to orient the implantable medical device in response to tension applied to the actuation line.

9. The system of claim 1, further comprising a removable lock wire configured to maintain coupling of the tether to the implantable medical device.

10. The system of claim 9, wherein the tether includes an eyelet and the removable lock wire is arranged through the eyelet to couple the removable lock wire to the tether.

11. The system of claim 10, wherein the eyelet of the tether is at or near a proximal end of the tether and a distal end of the tether is coupled to the actuation line.

12. The system of claim 11, wherein the removable lock wire is arranged through a flow lumen of the implantable medical device and the tether is arranged from the flow lumen of the implantable medical device at the proximal end of the tether to an exterior surface of the implantable medical device at the distal end of the tether.

13. The system of claim 12, wherein the tether is configured to release from the actuation line in response to withdraw of the removable lock wire from the eyelet of the tether.

14. The system of claim 9, further comprising a catheter arranged through a lumen of the implantable medical device, wherein a proximal end of the tether is releasably coupled to the catheter, and a distal end of the tether is coupled to the actuation line.

15. A system comprising:
a catheter;
an implantable medical device arranged near a leading end of the catheter and including a proximal end, a distal end, and a flow lumen extending therebetween;
a pivot forming a loop coupled to an exterior surface of the implantable medical device;
a sleeve coupled to the exterior surface of the implantable medical device proximal to the loop;
an actuation line arranged through a lumen defined by the sleeve; and
a tether coupled to the actuation line and arranged through the loop and configured to steer the implantable medical device in response to tension applied to the actuation line; wherein the tether is releasable from the pivot after the implantable medical device is oriented as desired.

16. The system of claim 15, wherein the loop and the sleeve are pivot points and are configured to form a pulley between the tether and the actuation line to steer the implantable medical device in response to tension applied to the actuation line.

17. The system of claim 15, further comprising a removable lock wire configured to maintain coupling of the tether to the implantable medical device, and wherein the tether is configured to release from the actuation line in response to withdraw of the removable lock wire.

18. A method of steering an implantable medical device, the method comprising:
delivering the implantable medical device to a target location within a patient's vasculature; and
manipulating an actuation line coupled to the implantable medical device by a tether arranged through a pivot forming a loop and coupled to an exterior surface of the implantable medical device to steer the implantable medical device; further including uncoupling the tether from the pivot after the implantable medical device is oriented.

19. The method of claim 18, further including maintaining coupling of the tether to the implantable medical device by a removable lock wire during the steering of the implantable medical device, and releasing the tether from the loop by withdrawing the removable lock wire.

* * * * *